United States Patent
Getin et al.

(10) Patent No.: US 7,075,641 B2
(45) Date of Patent: Jul. 11, 2006

(54) BIOSENSOR WITH AN ARBITRARY SUBSTRATE THAT CAN BE CHARACTERIZED IN PHOTOTHERMAL DEFLECTION

(75) Inventors: Stephane Getin, Grenoble (FR); Stephanie Gaugiran, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 317 days.

(21) Appl. No.: 10/735,681

(22) Filed: Dec. 16, 2003

(65) Prior Publication Data

US 2004/0135996 A1   Jul. 15, 2004

(30) Foreign Application Priority Data

Dec. 20, 2002 (FR) .................................. 02 16325

(51) Int. Cl.
*G01N 21/01* (2006.01)
(52) U.S. Cl. ....................... 356/244; 356/630
(58) Field of Classification Search ................ 356/244, 356/246, 432, 445, 630, 502, 504
See application file for complete search history.

(56) References Cited

U.S. PATENT DOCUMENTS

| 3,853,386 | A |   | 12/1974 | Ritter et al. |
| 4,528,464 | A | * | 7/1985  | Chemla et al. ............. 359/326 |
| 5,074,669 | A | * | 12/1991 | Opsal ........................ 356/445 |
| 5,604,581 | A | * | 2/1997  | Liu et al. ..................... 356/73 |
| 5,706,094 | A | * | 1/1998  | Maris ........................ 356/432 |
| 5,748,317 | A | * | 5/1998  | Maris et al. ................ 356/502 |
| 6,108,096 | A |   | 8/2000  | Ushio et al. |
| 6,504,618 | B1 | * | 1/2003 | Morath et al. ............. 356/630 |
| 6,801,322 | B1 | * | 10/2004 | Mautz ........................ 356/504 |

FOREIGN PATENT DOCUMENTS

| EP | 0 372 438 | 6/1990 |
| EP | 0 924 508 | 6/1999 |
| FR | 2 799 281 | 4/2001 |

* cited by examiner

*Primary Examiner*—Gregory J. Toatley, Jr.
*Assistant Examiner*—Sang H. Nguyen
(74) *Attorney, Agent, or Firm*—Oblon, Spivak, McClelland, Maier & Neustadt, P.C.

(57) ABSTRACT

The invention relates to a sample support designed to support a sample which is to be detected and/or analyzed by a photothermal detection method using an irradiation pump beam irradiating the sample and a detection and/or analysis probe beam. It comprises a substrate supporting a stack of thin dielectric layers forming a Bragg mirror on which the sample will be supported, the stack of thin dielectric layers being used to reflect the pump beam that reaches it.

The invention also relates to a device for detection and/or analysis of a sample by a photothermal method, the said device comprising a sample support according to the invention, a means of lighting the sample supported by the said support and supplying a pump beam, a means of detection and/or measurement of the absorption or reflection of the pump beam by the sample when it is illuminated by the said illumination means.

Finally, the invention relates to a particular application of the said device.

13 Claims, 1 Drawing Sheet

BIOSENSOR WITH AN ARBITRARY SUBSTRATE THAT CAN BE CHARACTERIZED IN PHOTOTHERMAL DEFLECTION

FIELD OF THE INVENTION

This invention relates to a sample support that can be used in a process for surface detection of absorbent components placed on the said sample support using photothermal deflection methods. The invention also relates to a photothermal detection device using the sample support according to the invention.

This invention may be applied to a surface analysis such as absorption mapping or thermal parameter imagery, and to the general domain of detection and analysis of a molecular recognition between a first and a second molecule, for example in molecular biology. Molecular recognition may be defined as being a specific interaction between two molecules being more or less complex, leading to a connection sufficiently stable between the two molecules, so that the molecules can be detected being bonded. For example, this could be a hybridisation of nucleic acids (DNA and/or RNA), an antigen/antibody type recognition reaction, a protein/protein type interaction, an enzyme/substrate type interaction, etc.

The device according to the invention will be used particularly in an application for the detection of oligonucleotide hybridisation on a solid support, in an aqueous medium or in air, for example for screening or for detection of hybridisation on a biochip.

STATE OF PRIOR ART

There are several methods for detecting absorbent substances on a surface. In particular, we will be interested in photothermal detection methods for which a complete presentation is given in the book by Bialkowski [1], which is referenced at the end of this description.

The photothermal deflection method is one photothermal detection method.

Consider a layer of an absorbent substance (called sample) to be studied, and deposited on a substrate. When this sample is irradiated by a light beam called a "pump" beam, it absorbs some of the incident light energy of the beam (the remainder of this light energy may, for example, be radiated or create fluorescence or a chemical reaction). This absorption will cause heating of the sample, which will heat the adjacent substrate and superstrate by thermal conduction. The temperature increase due to absorption is usually non-homogeneous and will therefore lead to an index gradient in the analysed medium and the adjacent media, the density of the media being made non-homogeneous by the temperature increase. A light beam called the "probe" beam" can be made to pass in the area in which the sample was irradiated, a deviation of the said beam will be observed due to the difference in index gradients. This deviation can be measured to quantify the gradient in question, and thus to deduce the temperature and absorption of the sample.

The advantage of the photothermal method is that it is only sensitive to absorption of the layer of the substance and not to its diffusion.

Furthermore, this technique is much more sensitive than the spectrophotometry method. The precision at which losses can be detected by absorption is of the order of one ppm, where "losses" means the ratio between the power absorbed by the sample and the received incident light power.

This photothermal method is frequently used in the biological detection field. It can be used to directly detect hybridisation of DNA that has strong absorption in the ultraviolet (see document [2]) or to qualify technological steps leading to the deposition of oligonucleotides on DNA biochips when in situ synthesis deposition technique is used (see document [3] referenced at the end of this description).

Nevertheless, for this method to be useable, the background noise caused by absorption of the substrate has to be limited. Light absorption by the substrate must be very weak so as not to "drown" the signal from substances to be analysed in the background noise induced by the substrate (see document [4] referenced at the end of this description).

It is found that substrates usually used in the biosensors domain (microscope slides made of float glass or silicon) are too absorbent and it is difficult to satisfy the conditions mentioned above using this type of substrate.

Therefore it is often necessary to use molten silica substrates with a very low absorption, but the price of those may be expensive, depending on the purity of the material.

For size reasons, these substrates are also badly adapted to production devices (for example, commercial synthesisers) and characterisation devices (confocal scanners) used by biologists.

Furthermore, existing devices have the disadvantage that powerful and frequently expensive laser sources have to be used for satisfactory detection of substances.

PRESENTATION OF THE INVENTION

The device according to the invention is intended to solve the disadvantages encountered in prior art.

This purpose is achieved using a sample support designed to support a sample which is to be detected and/or analysed by a photothermal detection method using a sample irradiation pump beam and a detection and/or analysis probe beam, characterised in that it comprises a substrate supporting a stack of thin dielectric layers forming a Bragg mirror on which the sample will be supported, the stack of thin dielectric layers being used to reflect the pump beam that reaches it.

Using the sample support according to the invention, the stack of thin optical layers or "Bragg" mirror reflects the pump beam signal such that the signal does not reach the absorbent substrate. Thus, there is no longer any need to worry about the absorption of the substrate, and any substrate can be used to support the sample. Note that elements to be analysed will be placed on the surface of the substrate-multi layer support, as shown in FIG. 2.

The multi layer or Bragg mirror deposit is characterised by the alternation of dielectric thin films that do not absorb light at the wavelength of the pump beam. These films will have high and low refraction indexes successively.

Advantageously, the Bragg mirror will include thin dielectric layers with a high refraction index formed from a material chosen from among the group composed of $TiO_2$, $HfO_2$, $SiO_3N_4$, $Ta_2O_5$, $Al_2O_3$ and $In_2O_3$.

Advantageously, the Bragg mirror will include thin dielectric layers with a low refraction index formed from a material chosen from among the group composed of $SiO_2$, $MgF_2$ and LiF.

The dielectric thin layers that are deposited on the substrate must also have a precise thickness to form a Bragg mirror. The thickness is calculated using the following formula:

$$e = \frac{\lambda'}{\frac{4n}{\cos(\theta)}}$$

where n is the index of the material considered, $\lambda'$ is the fictitious wavelength of the pump beam, $\theta$ is the angle between the beam in the layer considered and the normal to the stack.

And $$\lambda' = \lambda \left( \frac{\cos\theta_H + \cos\theta_B}{2} \right)$$

where $\lambda$ is the wavelength of the pump beam, $\theta_H$ is the angle between the pump beam and the normal in the high index layer, and $\theta_B$ is the angle between the pump beam and the normal in the low index layer.

The angle $\theta$ is calculated based on the Descartes laws using the following formula:

$$\theta = a\sin\left( \frac{n_{sup} \times \sin(\theta_{ref})}{N} \right)$$

where $\theta_{ref}$ is the angle of incidence of the pump beam in the medium in which the sample to be analysed is located and $n_{sup}$ is the refraction index of this medium. Depending on the case, N will be the refraction index of the high index layer when calculating the angle between the pump beam and the normal in the high index layer, or the refraction index of the low index layer when calculating the angle between the pump beam and the normal in the low index layer.

The dielectric thin layers may be deposited by PVD (Physical Vapor Deposition) or CVD (Chemical Vapor Deposition) or by a sol-gel method.

Advantageously, the upper layer forming the Bragg mirror is biocompatible with the sample that is to be fixed on the sample support.

The sample support thus made has the property of reducing or eliminating propagation of the pump beam to the substrate, and thus the background noise introduced by absorption of the substrate in supports according to prior art is limited or eliminated.

According to one particular embodiment of the invention, the upper layer forming the Bragg mirror is a layer with a low refraction index.

Made in this way, the device reinforces the light intensity at the surface close to substances to be detected, so that it is greater than for the bare substrate. This has two advantages:
  the detection sensitivity of the sample support according to the invention is higher than is possible with a substrate alone,
  the required intensity for the pump laser can be reduced.

The invention also relates to a device for detection and/or analysis of a sample by a photothermal method, the said device comprising a sample support according to the invention, a means of lighting the sample supported by the said support and supplying a pump beam, a means of detection and/or measurement of the absorption or reflection of the pump beam by the sample when it is illuminated by the said illumination means.

According to one particular embodiment of the invention, the device will also comprise a means of positioning the said detection and/or measurement means. The information obtained by this device is local, consequently the pump beam absorption or reflection detection and/or measurement means may be coupled to a system for displacement of the sample support relative to the pump beam. The assembly can then be used to compare values of the deviation of the probe beam between two points on the sample support, and in particular the signal may be represented in map form. According to the invention, the means of positioning the support may be any known means of precise displacement of the said sample support, for example micrometric translation and rotation plates.

Advantageously, the means of illuminating the sample and providing the pump beam will be a laser source.

Advantageously, the means of detection and/or measurement of absorption or reflection by the sample will comprise a light source supplying a probe beam and means of detecting or measuring the deviation of the probe beam.

Advantageously, the probe beam will be at a wavelength that is not absorbed by the sample. Similarly, the light source will advantageously be a laser source.

According to one particular embodiment of the invention, the means of detecting the deviation of the probe beam will comprise a multi-element photodiode or a simple photodiode. The multi-element photodiode can be chosen from among a group composed of a detector with two or four quadrants, a strip detector or a matrix detector, while the single photodiode will be partially covered by a mask or blade, or will only receive part of the probe beam.

The method of detecting absorbent components may be direct: the substance to be detected absorbs light sent on the sample if the operating wavelength of the device corresponds to the absorption wavelength of the substance. In other words, there will be absorption if the wavelength of the pump beam is chosen so that the sample is absorbent at this wavelength.

The detection method may also be indirect. In this case, substances to be detected will be equipped with markers that absorb light sent on the sample at the wavelength of the pump beam. In other words, the wavelength of the pump beam is chosen such that markers providing the sample are absorbent at this wavelength. For example, absorbent markers may be a colouring agent, metallic particles or quantum dots.

Finally, the invention relates to the use of this device for a test, a diagnosis or detection of oligonucleotide hybridisation, in a liquid medium or in air, on a solid support for "screening" purposes or for the detection of hybridisation on biochips.

BRIEF DESCRIPTION OF THE DRAWINGS

The invention will be better understood and other advantages and special features will become clear after reading the following description, given as a non-limitative example, accompanied by the attached drawings among which.

DETAILED DESCRIPTION OF EMBODIMENTS OF THE INVENTION

Figure 2:
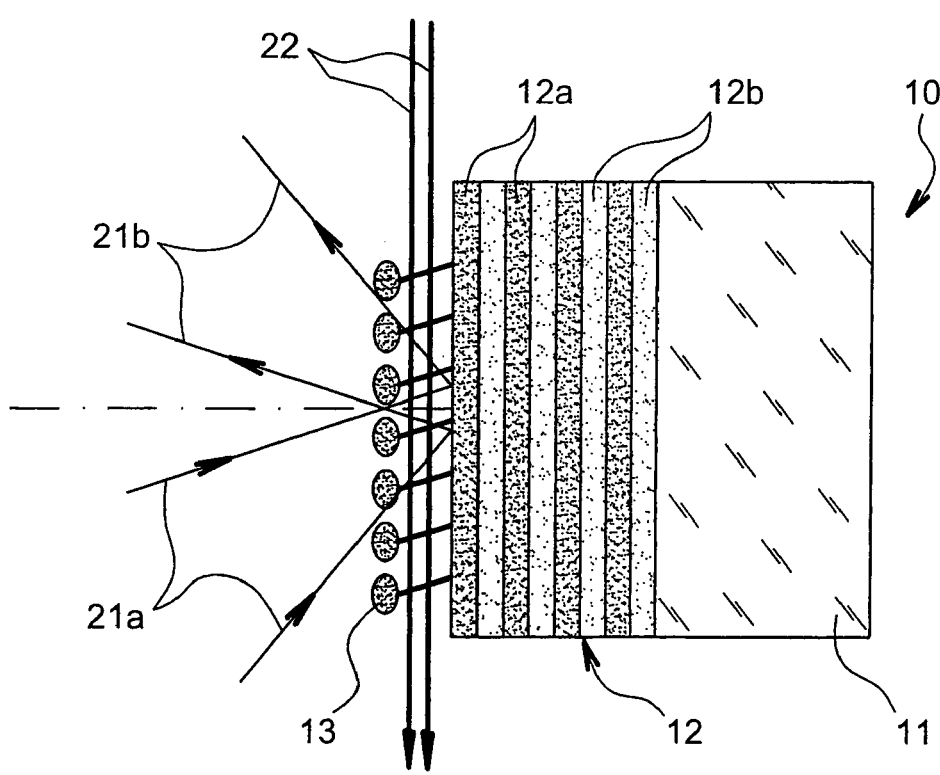
FIG. 2 is a diagram illustrating the photothermal deflection device with a substrate comprising a multi-layer according to the invention.

The orientation of the pump beam with respect to the probe beam may be chosen at leisure, for example as a function of the mechanical dimensions and/or to optimise the sensitivity by attempting to find the maximum absorption as a function of the angle of incidence. But concerning the probe beam, it is important that it should be placed so that it passes through the area in which the sample to be analysed has been irradiated by the pump beam. This crossing of the probe beam through gradients having different indexes will cause deviation of the said probe beam and thus enable measurement of absorption of the sample. In FIG. 2, the probe beam 22 is placed such that it grazes the surface of the sample support 10.

Figure 1:
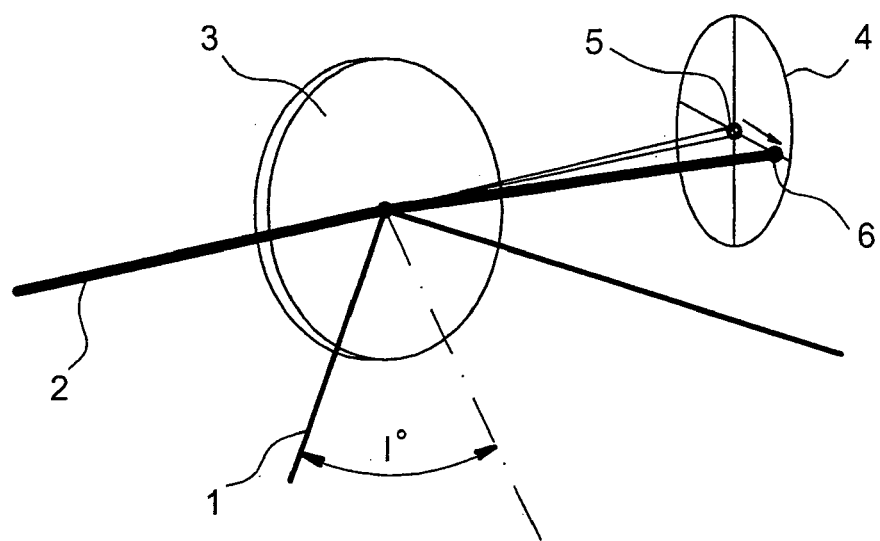
FIG. 1 is a diagram illustrating a possible configuration for an absorption measurement device by photothermal deflection.

In FIG. 1, the probe beam and the pump beam intersect to form a chosen angle. Reference 1 indicates the pump beam, reference 2 indicates the probe beam, reference 3 indicates the sample support on which the measurement sample is positioned, reference 4 represents a detector; reference 5 is a light spot formed by the probe beam on detector 4 when a non-absorbent reference sample is used, and reference 6 is a light spot formed by the probe beam on detector 4 when the sample to be analysed is used. It can clearly be seen that the probe beam was deviated between the two spots 5 and 6, which indicates that some of the pump beam was absorbed by the sample to be analysed.

FIG. 2 shows a detailed view of the photothermal deflection device using the sample support according to the invention. The sample support 10 is composed of a substrate 11 on which a multi-layer 12 has been deposited; the sample 13 to be analysed is placed on the multi-layer 12. An incident pump beam 21a is sent onto the sample 13 (part of the pump beam is reflected, see reference 21b) and the absorption of the sample is measured by measuring the deviation of a probe beam 22.

The substrate used according to the invention may be arbitrary insofar as the required thin layers can be deposited on it. For example, the substrate may be made of silicon or glass.

For example, for a pump beam with a wavelength $\lambda=514$ nm, the sample support will include a glass substrate and a multi-layer composed of alternating thin dielectric layers 12a made of silica with a thickness of 100 nm, and thin dielectric layers 12b made of hafnium dioxide with a thickness of 75 nm. This multi-layer will be composed of 20 thin layers.

BIBLIOGRAPHY

[1] S. E. BIALKOWSKI, Photothermal Spectroscopy Methods for Chemical Analysis, Wiley-Interscience Publication 1996, ISBN 0-471-57467-8.

[2] P. CHATON, L. POUPINET, F. GINOT, A. NOVELLI ROUSSEAU, Procédé et dispositif de détection d'une réaction de reconnaissance moléculaire (Process and device for detection of a molecular recognition reaction), patent application FR-A-2 799 281.

[3] P. CHATON, F. VINET, Procédé et dispositif d'analyse d'acides nucléiques fixés sur un support (Process and device for analysis of nucleic acids fixed on a support), patent application FR-A-2 799 282.

[4] ADELHELM et al, Development of a sensitive detection system based on the photothermal effect for biomolecular interaction studies, SPIE proceedings, vol. 2629, pages 325–333.

The invention claimed is:

1. A sample support designed to support a sample which is to be detected and/or analysed by a photothermal detection method using an irradiation pump beam irradiating the sample and a detection and/or analysis probe beam wherein said sample support comprises a substrate supporting a stack of thin dielectric layers forming a Bragg mirror on which the sample will be supported, the stack of thin dielectric layers being used to reflect the pump beam that reaches it.

2. A sample support according to claim 1, wherein the Bragg mirror includes thin dielectric layers with a high refraction index, formed from a material selected from the group consisting of $TiO_2$, $HfO_2$, $SiO_3N_4$, $Ta_2O_5$, $Al_2O_3$ and $In_2O_3$.

3. A sample support according to claim 1, wherein the Bragg mirror includes thin dielectric layers with a low refraction index, formed from a material selected from the group consisting of $SiO_2$, $MgF_2$ and LiF.

4. A sample support according to claim 1, wherein the upper layer forming the Bragg mirror is biocompatible with the sample.

5. A sample support according to claim 1, characterized in that wherein the upper layer forming the Bragg mirror is a layer with a low refraction index.

6. A device for detection and/or analysis of a sample by a photothermal method, said device comprising a sample support according to claim 5, a means of lighting the sample supported by said support and supplying, a pump beam, a means of detection and/or measurement of the absorption or reflection of the pump beam by the sample when it is illuminated by said illumination means.

7. A device according to claim 6 further comprising means of positioning the said detection and/or measurement means.

8. A device according to claim 6, wherein the means of illuminating the sample and providing the pump beam is a laser source.

9. A device according to claim 6, wherein the means of detection and/or measurement of absorption or reflection of the pump beam by the sample comprises a light source supplying a probe beam and means of detecting the deviation of the probe beam.

10. A device according to claim 9 the previous claim, wherein the means of detecting the deviation of the probe beam comprise a multi-element photodiode or a simple photodiode.

11. A device according to claim 6, wherein the wavelength of the pump beam is chosen so that the sample is absorbent at this wavelength.

12. A device according to claim 6, wherein the wavelength of the pump beam is chosen so that markers provided on the sample absorb light at this wavelength.

13. Use of the device according to claim 6 for a test, a diagnosis or detection of oligonucleotide hybridisation, in a liquid medium or in air, on a solid support for "screening" purposes or for the detection of hybridisation on biochips.

* * * * *